(12) United States Patent
Chodoeva

(10) Patent No.: US 11,351,145 B2
(45) Date of Patent: Jun. 7, 2022

(54) QUERCETIN-BASED COMPOSITION FOR TREATING RHINOSINUSITIS

(71) Applicant: APHABIO THERAPEUTICS, Toulenne (FR)

(72) Inventor: Ainura Chodoeva, Toulenne (FR)

(73) Assignee: APHABIO THERAPEUTICS, Toulenne (FR)

( * ) Notice: Subject to any disclaimer, the term of this patent is extended or adjusted under 35 U.S.C. 154(b) by 0 days.

(21) Appl. No.: 16/766,404

(22) PCT Filed: Nov. 22, 2018

(86) PCT No.: PCT/EP2018/082241
§ 371 (c)(1),
(2) Date: May 22, 2020

(87) PCT Pub. No.: WO2019/101867
PCT Pub. Date: May 31, 2019

(65) Prior Publication Data
US 2021/0000787 A1    Jan. 7, 2021

(30) Foreign Application Priority Data

Nov. 23, 2017 (FR) ...................................... 1771251

(51) Int. Cl.
| | |
|---|---|
| *A61K 31/352* | (2006.01) |
| *A61P 11/02* | (2006.01) |
| *A61K 9/00* | (2006.01) |
| *A61K 9/08* | (2006.01) |
| *A61K 31/192* | (2006.01) |
| *A61K 31/365* | (2006.01) |
| *A61K 31/7048* | (2006.01) |
| *A61K 36/8962* | (2006.01) |
| *A61K 47/02* | (2006.01) |
| *A61K 47/22* | (2006.01) |
| *A61K 45/06* | (2006.01) |

(52) U.S. Cl.
CPC .......... *A61K 31/352* (2013.01); *A61K 9/0043* (2013.01); *A61K 9/08* (2013.01); *A61K 31/192* (2013.01); *A61K 31/365* (2013.01); *A61K 31/7048* (2013.01); *A61K 36/8962* (2013.01); *A61K 47/02* (2013.01); *A61K 47/22* (2013.01); *A61P 11/02* (2018.01); *A61K 45/06* (2013.01); *A61K 2236/331* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 5,977,184 | A | * | 11/1999 | Birdsall ............... A61K 31/352 514/685 |
| 2013/0156871 | A1 | | 6/2013 | Keller |
| 2014/0199266 | A1 | * | 7/2014 | Park ..................... A61K 35/644 424/93.1 |

FOREIGN PATENT DOCUMENTS

KR      20010082121 A      8/2001

OTHER PUBLICATIONS

Khiari, Z., & Makris, D. P. (2012). Stability and transformation of major flavonols in onion (*Allium cepa*) solid wastes. Journal of food science and technology, 49(4), 489-494. (Year: 2012).*
Kashiwabara, M., Asano, K., Mizuyoshi, T., & Kobayashi, H. (2016). Suppression of neuropeptide production by quercetin in allergic rhinitis model rats. BMC Complementary and Alternative Medicine, 16(1), 1-9. (Year: 2016).*
Gülşen, A., Turan, B., Makris, D. P., & Kefalas, P. (2007). Copper (II)-mediated biomimetic oxidation of quercetin: generation of a naturally occurring oxidation product and evaluation of its in vitro antioxidant properties. European Food Research and Technology, 225(3), 435-441. (Year: 2007).*
Atala, E., Fuentes, J., Wehrhahn, M. J., & Speisky, H. (2017). Quercetin and related flavonoids conserve their antioxidant properties despite undergoing chemical or enzymatic oxidation. Food chemistry, 234, 479-485. (Year: 2017).*
Kwak et al., "Variation of Quercetin Glycoside Derivatives in 3 Onion (*Allium Cepa* L.) Varieties", Saudi Journal of Biololgical Sciences, May 27, 2016, pp. 1-5, vol. 24.
Thornhill, et al., "Natural Treatment of Perennial Allergic Rhinitis", Alternative Medicine Review, 2000, pp. 448-454, vol. 5, No. 5.
Ariano, "Efficacy of a novel food supplement in the relief of the signs and symptoms of seasonal allergic rhinitis and in the reduction of the consumption of anti-allergic drugs", Acta, Biomed, Apr. 27, 2015, pp. 53-58, vol. 86, No. 1.
Sagit et al., "Effectiveness of Quercetin in an Experimental Rat Model of Allergic Rhinitis", European Arch. Otorhinolaryngol., May 10, 2017, pp. 3087-3095, vol. 274.
Mintel, "Onion Soup & Dip Mix", GNPD, Oct. 2017 (Oct. 2017), Database accession No. 5194745 Retrouvé de : URL:MINTEL XP002783219.

* cited by examiner

*Primary Examiner* — Dale R Miller
(74) *Attorney, Agent, or Firm* — Greer, Burns & Crain, Ltd.

(57) ABSTRACT

The present invention concerns compositions for rinsing the nasal cavity and the sinus cavities for curative or prophylactic treatments of acute and/or chronic rhinitis, and acute and/or chronic sinusitis, comprising:
sodium chloride and/or potassium chloride; quercetin, and at least one active agent of the polyphenolic group chosen from the compounds: quercetin-4'-glycoside, 2-(3,4-dihydroxy-benzoyl)-2,4,6-trihydroxy-3(2H)-benzofuranone, protocatechuic acid; and wherein the quercetin is in the anhydrous form with an approximate molecular mass of 302 g/mol, or in the form of quercetin hydrate with an approximate molecular mass of 320 g/mol, or in the form of quercetin dihydrate with an approximate molecular mass of 338 g/mol.
The present invention also relates to the methods for preparing these compositions and the method for treating acute and chronic rhinosinusitis using these compositions.

15 Claims, No Drawings

QUERCETIN-BASED COMPOSITION FOR TREATING RHINOSINUSITIS

CROSS-REFERENCE TO RELATED APPLICATIONS

This application is the U.S. National phase application corresponding to PCT/EP2018/082241 which was assigned an international filing date of Nov. 22, 2018 and associated with publication WO 2019/101867 A1 and which claims priority to FR 1771251 filed on Nov. 23, 2017, the disclosures of which are expressly incorporated herein by reference.

TECHNICAL FIELD

The present invention relates to a particular composition and its use in the treatment of rhinosinusitis. The invention also relates to a method for obtaining such a composition.

Rhinosinusitis (RS) is an inflammation of the nasal cavity and paranasal sinuses characterized by nasal obstruction/congestion or nasal discharge, facial pain and pressure, reduction or loss of smell and/or mucopurulent discharge primarily from the middle meatus, oedema/mucosal obstruction primarily in the zone of the middle meatus.

Rhinosinusitis is classified into acute RS (ARS) with the duration of the disease<12 weeks, chronic RS (CRS) with the duration>12 weeks, with nasal polyps (CRSwNP) or without nasal polyps (CRSsNP).

Within this invention, the term "rhinosinusitis" encompasses all forms of disease, comprising acute and chronic rhinitis and acute and chronic sinusitis with or without nasal polyps.

BACKGROUND

The International Disease Classification published by the WHO does not contain the term Rhinosinusitis as the disease unit. Instead, acute (J30) and chronic (J31) rhinitis, acute (J01) and chronic (J32) sinusitis have been classified separately (IDC WHO, http://apps.who.int/classifications/icd10/browse/2016/en#/J30-J39). Nevertheless, the European Academy of Allergology and Clinical Immunology, European Rhinologic Society and the American Academy of Otolaryngology—Head and Neck Surgery Foundation, publishing the guidelines for the management of rhinosinusitis, have agreed to use the term "rhinosinusitis". Yet in most cases, sinusitis and rhinitis are concomitant diseases, always co-existing together. "The widespread adoption of the term 'rhinosinusitis' in preference to 'sinusitis' indirectly supports the perspective that the foreign material brought in through the airway, or perhaps, from the nasopharynx, acts on the nasal mucosa first, with direct and indirect secondary effects on the sinus mucosa" (European Position Paper on Rhinosinusitis and Nasal Polyps 2012; Rhinology supplement 23:1-298, 2012).

Rhinosinusitis is one of the most widespread diseases in the world, with a mean prevalence of more than 10% of the world population.

In the US, rhinosinusitis affects 1 in 8 people, with an annual healthcare cost exceeding $11 billion (Rosenfeld, R M et al. Clinical Practice Guideline (Update): Adult Sinusitis. Otolaryngology-Head and Neck Surgery Vol. 152(2S), 2015, pp 1-39). The total cost of treating a patient with CRS was $2609 per year in US; the total cost of a patient treated in a university hospital for chronic rhinosinusitis was $1861/year in Europe. Rhinosinusitis is one of the most costly health conditions to US employers. Among chronic illnesses, total healthcare costs and household healthcare expenditures are higher for patients with rhinosinusitis. A major component of the indirect costs result from absenteeism (missed workdays) and presenteeism (decreased productivity at work). Research provided by the National Health Interview Survey between 1997 and 2006 encompassing nearly 315,000 individuals reported that American patients with rhinosinusitis missed on average 5.7 days of work per year (European Position Paper on Rhinosinusitis and Nasal Polyps 2012; Rhinology supplement 23:1-298, 2012).

Currently, no specific treatment exists for the management of rhinosinusitis. Some antibiotics have a labeled indication for acute bacterial rhinosinusitis; other groups of drugs, such as corticosteroids, antihistamines, alpha-adrenergic decongestants are recommended, but none of them are approved by the FDA (Guidance for Industry. Sinusitis: Designing Clinical Development Programs of Nonantimicrobial Drugs for Treatment. U.S. DHHS FDA Center for Drug Evaluation and Research November 2006).

Guidelines for the treatment of Rhinosinusitis are developed by international expert groups, such as the European Academy of Allergy and Clinical Immunology and the European Rhinologic Society.

According to the protocol established by these associations (European Position Paper on Rhinosinusitis and Nasal Polyps 2012; Rhinology supplement 23:1-298, 2012), the different forms of rhinosinusitis are managed as follows:

Acute rhinosinusitis (<12 weeks): The initial treatment is a symptomatic therapy: analgesics, saline irrigations, antihistamines, decongestants may be proposed despite the lack of evidence of their effectiveness. If no improvement in 7-14 days, intranasal corticoids are recommended. In the case of bacterial RS complication, it is recommended to prescribe first-line antibiotics (amoxicillin alone or with clavulanic acid). Radiology imaging must be done simultaneously to confirm bacterial rhinosinusitis and to verify the absence of complication. If no efficacy is observed, antibiotics are changed (e.g., macrolides). In the case of treatment failure, continuation of topical intranasal corticoids and/or surgical interventions may be recommended.

Chronic rhinosinusitis (>12 weeks): Independently of the presence or absence of nasal polyps, the treatment protocol is as follows: After endoscopic examinations and CT scan, intra-nasal corticosteroids are prescribed. If no improvement after 3 months, a long-term antibiotic therapy is added. If still no improvement, a surgical intervention is recommended.

The efficacy of intranasal corticosteroids is very limited: they are effective in one person out of 14 treated (Hayward, G et al. Intranasal Corticosteroids in Management of Acute Sinusitis: A Systematic Review and Meta-Analysis. Ann Fam Med Vol. 10: 2012, pp 241-249).

Clinicians are strongly advised to weigh the moderate benefits of antibiotic treatment against the potential for adverse effects before prescribing of antibiotics. Moreover, the most recent American guidelines recommend "watchful waiting" before initiating antibiotic therapy, even if the bacterial origin of rhinosinusitis is confirmed, due to low efficacy of antibiotics against RS: they are effective in 1 out of 20 persons treated (Rosenfeld, R M et al. Clinical Practice Guideline (Update): Adult Sinusitis. Otolaryngology-Head and Neck Surgery Vol. 152(2S), 2015, pp 1-39).

Topical decongestants may be used for palliative treatment, but continuous administration (longer than 3-5 days) may cause rhinitis medicamentosa.

Isotonic or hypertonic saline solutions for nasal irrigation are widely used in daily hygiene practice. In general, physiological saline solution is mostly used. The volume of solution for nasal irrigation varies from 5 mL to 500 mL. The effect of isotonic saline solution is explained by its ability to remove the irritating foreign matters and inflammatory mediators from the nasal cavity. Currently, several nasal formulations containing buffer solutions are being developed. One of the formulations for nasal irrigation was developed by Ted Keller (US2013/0156871, Ted Keller, Jun. 20, 2013), where he discovered the nasal solution comprising sodium chloride and a buffer composed of sodium ascorbate and sodium bicarbonate. After dissolution in water, this composition may be used to cleanse the nasal and sinus cavities. However, like the many existing solutions, such a composition is not satisfactory and is not sufficient for treatment of rhinosinusitis.

SUMMARY

The aim of the present invention is to address the problems of the existing solutions and to provide the compositions for cleaning the nasal and sinus cavities to effectively treat acute and chronic rhinosinusitis. To that end, the invention relates to compositions comprising a salt; and active agents of the polyphenolic group selected from: quercetin, quercetin-4'-glycoside, 2-(3,4-dihydroxybenzoyl)-2,4,6-trihydroxy-3(2H)-benzofuranone, protocatechuic acid, and may contain impurities derived from quercetin, including quercetin-3'-glycoside, quercetin-7'-glycoside, diglycosides and triglycosides of quercetin, quercetin dimers, in an amount less than 5% by weight of the total amount of the active agents.

According to the present invention, it is necessary to combine quercetin with quercetin derivatives such as quercetin-4'-glycoside, 2-(3,4-dihydroxybenzoyl)-2,4,6-trihydroxy-3(2H)-benzofuranone, protocatechuic acid. This combination provides a synergistic effect that increases the effectiveness of the composition in the treatment of rhinosinusitis.

The invention also relates to the use of these compositions for the prevention and treatment of rhinosinusitis.

Lastly, another aim of the invention is to provide a method for the preparation of these compositions.

DETAILED DESCRIPTION

Definitions

The term "active agent" in this invention means the compound or ingredient producing the desired therapeutic effect.

The term "impurity" in this invention refers to the compound or ingredient without therapeutic effect, concomitant with active agents, present in the composition of a drug in minor quantities.

The "therapeutically effective amount" in this invention means the amount of active agent that may produce the therapeutic effect in the treated subjects.

The terms "patient" or "subject" in this invention refer to a mammal, comprising an animal or a human, to whom the present invention may be applied.

The subject matter of the invention is a composition for rinsing the nasal and sinus cavities for prophylaxis or treatment of acute and chronic rhinitis and acute and chronic sinusitis, comprising:
sodium chloride and/or potassium chloride;
quercetin, and
at least one active agent of the polyphenolic group selected from: quercetin-4'-glycoside, 2-(3,4-dihydroxybenzoyl)-2,4,6-trihydroxy-3(2H)-benzofuranone, protocatechuic acid; and
wherein quercetin is in the anhydrous form with an approximate molecular mass of 302 g/mol, or as a quercetin hydrate with an approximate molecular mass of 320 g/mol, or as a quercetin dihydrate with an approximate molecular mass of 338 g/mol.

The invention relates to nasal compositions, containing active ingredients with a proven efficacy for the treatment of rhinosinusitis.

According to the invention, the molecules of the composition may be extracted from the onion peel. The efficacy of the crude extract and compounds purified from it was studied on animal models with experimentally-induced rhinosinusitis. The results of this invention are described in examples. The results of this research prove the effectiveness of the onion peel extract and compounds isolated from it: quercetin, quercetin-4'-glycoside, 2-(3,4-dihydroxybenzoyl)-2,4,6-trihydroxy-3(2H)-benzofuranone and protocatechuic acid for rhinosinusitis. These results also made it possible to develop the formulations containing these agents, and to develop the methods of treatment.

Depending on the extraction and preparation conditions, quercetin may be used in the anhydrous form, with an approximate molecular mass of 302 g/mol, or in the form of quercetin hydrate with an approximate molecular mass of 320 g/mol, or in the form of quercetin dihydrate, with an approximate molecular mass of 338 g/mol.

According to the invention, several varieties of compositions are possible.

1. Nasal Composition. Comprising the Salt and Quercetin, Quercetin-4'-Glycoside, 2-(3,4-Dihydroxybenzoyl)-2,4,6-Trihydroxy-3(2H)-Benzofuranone and Protocatechuic Acid According to one embodiment, the nasal formulation comprises the salt and an extract of plants containing flavonoids: quercetin, quercetin-4'-glycoside, 2-(3,4-dihydroxybenzoyl)-2,4,6-trihydroxy-3(2H)-benzofuranone and protocatechuic acid. The salt may be sodium chloride or potassium chloride, or both, in quantity sufficient to produce the hypotonic, isotonic or hypertonic solution. The amount of salt may be between 83-99.77% by weight of the dry composition. The amount of quercetin in the dry composition may be between 0.23-3% by weight. The amount of quercetin-4'-glycoside in the dry composition may be between 0.000001-3% by weight. The amount of 2-(3,4-dihydroxybenzoyl)-2,4,6-trihydroxy-3(2H)-benzofuranone in the dry composition may be between 0.000001-3% by weight. The amount of protocatechuic acid in the dry composition may be between 0.000001-3% by weight.

According to one embodiment, the active agent comprising quercetin, quercetin-4'-glycoside, 2-(3,4-dihydroxybenzoyl)-2,4,6-trihydroxy-3(2H)-benzofuranone and protocatechuic acid may be prepared by the method of extraction from plants containing flavonoids, for example from onion peel. The method of preparing of the extract containing active agents may comprise the following stages:

mixing the powdered onion peel with cold water in a proportion of 0.1-2 g/50 mL (m/v);

bringing the mixture to a boil, and simmering for 30 min at boiling temperature;

cooling the mixture, filtering and freeze-drying it.

This method makes it possible to obtain a crude extract composed of the active agents: quercetin, 2-(3,4-dihydroxybenzoyl)-2,4,6-trihydroxy-3(2H)-benzofuranone, quercetin-4'-glycoside and protocatechuic acid. The crude extract may also contain other impurities derived from quercetin, for example, quercetin-3'-glycoside, quercetin-7'-glycoside, diglycosides and triglycosides of quercetin, quercetin dimers, in an amount not exceeding 5% of the total weight of active agents.

Another extraction method consists of using of organic solvents, preferably methanol or ethanol diluted with water, in a ratio between 50/50 and 90/10 (v/v). According to this method, the defined amount of powdered onion peel is mixed with the organic solvent in a proportion of 1-10 g/30 mL (m/v), and stirred for 24 hours at a room temperature. The obtained solution is filtered, then evaporated to dryness. The crude extract obtained may be separated by the high-performance liquid chromatography method.

The separation conditions may be as follows:

50 mg to 200 mg of crude extract is injected into a Phenomenex C18 column (21.2 mm×150 mm, 5 µm, 100 A) of the HPLC apparatus. The following solvents may be used: Solvent A: H20/TFA 0.5% (1 L/5 mL); Solvent B: ACN. The flow may be: 15 mL/min.

Qualitative and quantitative analyses of the compositions may be performed by the UPLC-DAD-MS techniques (Agilent technologies, USA). The elution conditions may be as follows: 1 µL of the solution is injected into the Agilent C18 column (2.1 mm, 1.8 µm) of the UPLC at the temperature of 25° C. The solvents used may be: Solvent A: $H_2O$/HCOOH 0.1% and Solvent B: ACN/HCOOH 0.1%. The flow may be: 0.4 mL/min. The isolated compounds may be detected first by the diode array detector, then by the Mass-Spectrometer analyzer. Mass-Spectrometry analyses may be performed in negative or positive mode. The separation and analysis techniques using the UPLC-DAD-MS method may be the same for all of the compositions.

According to one embodiment, the composition may be prepared by mixing the commercially-available compounds: quercetin, 2-(3,4-dihydroxybenzoyl)-2,4,6-trihydroxy-3(2H)-benzofuranone, quercetin-4'-glycoside, protocatechuic acid and the salt selected from sodium chloride or potassium chloride.

The dry composition may be prepared by one of the following methods:

a). Dissolution of quercetin, 2-(3,4-dihydroxybenzoyl)-2,4,6-trihydroxy-3(2H)-benzofuranone, quercetin-4'-glycoside, protocatechuic acid and the salt in the water heated to 80-100° C. Then the solution is cooled to room temperature, frozen and freeze-dried.

b). Dissolution of quercetin, 2-(3,4-dihydroxybenzoyl)-2,4,6-trihydroxy-3(2H)-benzofuranone, quercetin-4'-glycoside, protocatechuic acid in the water heated to 80-100° C. Then the solution is cooled to room temperature, the salt is added and dissolved. Then the solution is frozen and freeze-dried.

c). Quercetin, 2-(3,4-dihydroxybenzoyl)-2,4,6-trihydroxy-3(2H)-benzofuranone, quercetin-4'-glycoside and protocatechuic acid are dissolved in the organic solvent, preferably in ethanol or methanol diluted with water. The organic solvent/water ratio may be between 50/50 and 90/10 (v/v). The salt is dissolved in the water. Then, the two solutions are mixed at room temperature, frozen and freeze-dried.

d). Powders of quercetin, 2-(3,4-dihydroxybenzoyl)-2,4,6-trihydroxy-3(2H)-benzofuranone, quercetin-4'-glycoside and protocatechuic acid are mixed with sodium chloride or potassium chloride.

The composition may be sterilized or not, may be provided in the dry or liquid form, distributed in single-dose or multi-dose containers.

The composition may include one or more biologically active ingredients consistent with therapy and additives selected from pharmaceutical carriers, stabilizers, surfactants, preservatives, and essential oils. The biologically active ingredients may be selected from antibiotics, corticosteroids, and/or copper, manganese and sulfur salts. The essential oils may be chosen from eucalyptus oil, rosemary oil, tea tree oil or menthol.

According to one embodiment, the dry composition may subsequently be mixed with water.

The obtained solution or suspension comprises sodium chloride and/or potassium chloride in concentration 0.4-2% by weight, quercetin in concentration 0.0023-0.03% by weight, quercetin-4'-glycoside in concentration 0.00000001-0.03% by weight, 2-(3,4-dihydroxybenzoyl)-2,4,6-trihydroxy-3(2H)-benzofuranone in concentration 0.00000001-0.03% by weight and protocatechuic acid in concentration 0.00000001-0.03% by weight and may contain other impurities, derived from quercetin up to 0.5% by total weight of the active agents.

According to another embodiment, the dry composition may be mixed with the solution containing the bicarbonate salt. The bicarbonate salt may be sodium bicarbonate or potassium bicarbonate or both. The bicarbonate salt concentration may vary up to 0.5%, preferably between 0.1%-0.5% by weight, more preferably 0.25-0.5% by weight. The temperature of the water or bicarbonate solution may be between 30° C. and 38° C. At this temperature, certain compounds, for example quercetin, may remain in suspension, others may be dissolved completely. According to one particular variant, the water may be boiled and then cooled to 37° C. before mixing.

The water used for the preparation of the liquid composition may be distilled, deionized, purified and sterilized.

Although the use of preservatives and other excipients in the composition is not excluded, the sterile preparations without preservatives may be produced. This makes it possible to keep the compositions in sterile conditions and to limit the adverse effects due to the presence of preservatives. The blow-fill-seal technique, using unidose plastic containers or pre-filled syringes under aseptic conditions, may be preferred.

In one embodiment, the composition may be presented as follows:

Composition consisting of two parts:

part A: containing the dry powder, comprising sodium chloride or potassium chloride, quercetin, 2-(3,4-dihydroxybenzoyl)-2,4,6-trihydroxy-3(2H)-benzofuranone, quercetin-4'-glycoside and protocatechuic acid.

part B: containing 20 mL of water or sodium bicarbonate or potassium bicarbonate solution.

2. Nasal Composition, Comprising the Salt and Quercetin, Quercetin-4'-Glycoside and Protocatechuic Acid According to one embodiment, the nasal formulation comprises salt and an extract of plants containing flavonoids: quercetin, quercetin-4'-glycoside and protocatechuic acid. The salt may be sodium chloride or potassium chloride, or both, in quantity sufficient to produce the hypotonic, isotonic or hypertonic solution. The amount of salt may be between 86-99.77% by weight of the dry composition. The amount of quercetin in the dry composition may be between 0.23-3% by weight. The amount of quercetin-4'-glycoside in the dry composition may be between 0.000001-3% by weight. The amount of protocatechuic acid in the dry composition may be between 0.000001-3% by weight.

According to one embodiment, the active agent comprising quercetin, quercetin-4'-glycoside and protocatechuic acid may be prepared by the method of extraction from plants containing flavonoids, for example from onion peel. The method of preparing the extract containing active agents may comprise the following stages:

mixing the powdered onion peel with cold water in a proportion of 0.1-2 g/50 mL (m/v);

bringing the mixture to a boil, and simmering for 30 min at boiling temperature;

cooling the mixture, filtering and freeze-drying it.

This method makes it possible to obtain a crude extract composed of the active agents: quercetin, quercetin-4'-glycoside and protocatechuic acid. The crude extract may also contain other impurities derived from quercetin, for example, quercetin-3'-glycoside, quercetin-7'-glycoside, diglycosides and triglycosides of quercetin, quercetin dimers, in an amount not exceeding 5% of the total weight of active agents.

Another extraction method consists of using of organic solvents, preferably methanol or ethanol diluted with water in a ratio between 50/50 and 90/10 (v/v). According to this method, the defined amount of powdered onion peel is mixed with the organic solvent in a proportion of 1-10 g/30 mL (m/v), and stirred for 24 hours at room temperature. The solution obtained is filtered, then evaporated to dryness. The crude extract obtained may be separated by the high-performance liquid chromatography method.

The separation conditions may be as follows:

50 mg to 200 mg of crude extract is injected into a Phenomenex C18 column (21.2 mm×150 mm, 5 μm, 100 A) of the HPLC apparatus. The following solvents may be used: Solvent A: H20/TFA 0.5% (1 L/5 mL); Solvent B: ACN. The flow may be: 15 mL/min.

Qualitative and quantitative analyses of the compositions may be performed by the UPLC-DAD-MS techniques (Agilent technologies, USA). The elution conditions may be as follows: 1 μL of the solution is injected into the Agilent C18 column (2.1 mm, 1.8 μm) of the UPLC at the temperature of 25° C. The solvents used may be: Solvent A: $H_2O$/HCOOH 0.1% and Solvent B: ACN/HCOOH 0.1%. The flow may be: 0.4 mL/min. The isolated compounds may be detected first by the diode array detector, then by the Mass-Spectrometer analyzer. Mass Spectrometry analyses may be performed in negative or positive mode. The separation and analysis techniques by the UPLC-DAD-MS method may be the same for all of the compositions.

According to one embodiment, the composition may be prepared by mixing the commercially-available compounds: quercetin, quercetin-4'-glycoside, protocatechuic acid and the salt selected from sodium chloride or potassium chloride.

The dry composition may be prepared by one of the following methods:

a). Dissolution of quercetin, quercetin-4'-glycoside, protocatechuic acid and salt in water heated to 80-100° C. Then the solution is cooled to room temperature, frozen and freeze-dried.

b). Dissolution of quercetin, quercetin-4'-glycoside, protocatechuic acid in water heated to 80-100° C. Then the solution is cooled to room temperature, and the salt is added and dissolved. Then the solution is frozen and freeze-dried.

c). Quercetin, quercetin-4'-glycoside and protocatechuic acid are dissolved in the organic solvent, preferably in ethanol or methanol diluted with water. The organic solvent/water ratio may be between 50/50 and 90/10 (v/v). The salt is dissolved in the water. Then, the two solutions are mixed at room temperature, frozen and freeze-dried.

d). Powders of quercetin, quercetin-4'-glycoside and protocatechuic acid are mixed with sodium chloride or potassium chloride.

The composition may be sterilized or not, may be provided in the dry or liquid form, distributed in single-dose or multi-dose containers. The composition may include one or more biologically active ingredients consistent with therapy and additives selected from pharmaceutical carriers, stabilizers, surfactants, preservatives, and essential oils. The biologically active ingredients may be selected from antibiotics, corticosteroids, and/or copper, manganese and sulfur salts. The essential oils may be chosen from eucalyptus oil, rosemary oil, tea tree oil or menthol.

According to one embodiment, the dry composition may subsequently be mixed with water.

The obtained solution or suspension comprises sodium chloride and/or potassium chloride in concentration 0.4-2% by weight, quercetin in concentration 0.0023-0.03% by weight, quercetin-4'-glycoside in concentration 0.00000001-0.03% by weight, and protocatechuic acid in concentration 0.00000001-0.03% by weight and may contain other impurities derived from quercetin up to 0.5% by total weight of the active agents.

According to another embodiment, the dry composition may be mixed with the solution containing the bicarbonate salt. The bicarbonate salt may be sodium bicarbonate or potassium bicarbonate or both. The bicarbonate salt concentration may vary up to 0.5%, preferably between 0.1%-0.5% by weight, more preferably 0.25-0.5% by weight. The temperature of the water or bicarbonate solution may be between 30° C. and 38° C. At this temperature, certain compounds, for example quercetin, may remain in suspension, others may be dissolved completely. According to one particular variant, the water may be boiled and then cooled to 37° C. before mixing.

The water used for the preparation of the liquid composition may be distilled, deionized, purified and sterilized.

Although the use of preservatives and other excipients in the composition is not excluded, sterile preparations without preservatives may be produced. This makes it possible to keep the compositions in sterile conditions and to limit the adverse effects due to the presence of preservatives. The blow-fill-seal technique, using unidose plastic containers or pre-filled syringes under aseptic conditions, may be preferred.

In one embodiment, the composition may be presented as follows:

Composition consisting of two parts:

part A: containing the dry powder, comprising sodium chloride or potassium chloride, quercetin, quercetin-4'-glycoside and protocatechuic acid.

part B: containing 20 mL of water or sodium bicarbonate or potassium bicarbonate solution.

3. Nasal Composition, Comprising the Salt and Quercetin, 2-(3,4-dihydroxybenzoyl)-2,4,6-trihydroxy-3(2H)-benzofuranone and Protocatechuic Acid According to one embodiment, the nasal formulation comprises salt, quercetin, 2-(3,4-dihydroxybenzoyl)-2,4,6-trihydroxy-3(2H)-benzofuranone and protocatechuic acid. The salt may be sodium chloride or potassium chloride, or both, in quantity sufficient to produce the hypotonic, isotonic or hypertonic solution. The amount of salt may be between 91-99.77% by weight of the dry composition. The amount of quercetin in the dry composition may be between 0.23-3% by weight. The amount of 2-(3,4-dihydroxybenzoyl)-2,4,6-trihydroxy-3(2H)-benzofuranone in the dry composition may be between 0.000001-3% by weight. The amount of protocatechuic acid in the dry composition may be between 0.000001-3% by weight.

According to one embodiment, the active agent comprising quercetin, 2-(3,4-dihydroxybenzoyl)-2,4,6-trihydroxy-3 (2H)-benzofuranone and protocatechuic acid may be prepared by the method of extraction from plants containing flavonoids, for example from onion peel. The method of preparing the extract containing active agents may comprise the following stages:

mixing the powdered onion peel with cold water in a proportion of 0.1-2 g/50 mL (m/v);

bringing the mixture to a boil, and simmering for 30 min at boiling temperature;

cooling the mixture, filtering and freeze-drying it.

This method makes it possible to obtain a crude extract composed of the active agents: quercetin, 2-(3,4-dihydroxybenzoyl)-2,4,6-trihydroxy-3(2H)-benzofuranone, quercetin-4'-glycoside and protocatechuic acid. The crude extract may also contain other impurities derived from quercetin, for example, quercetin-3'-glycoside, quercetin-7'-glycoside, diglycosides and triglycosides of quercetin, quercetin dimers, in an amount not exceeding 5% of the total weight of active agents.

Another extraction method consists of using of organic solvents, preferably methanol or ethanol diluted with water in a ratio between 50/50 and 90/10 (v/v). According to this method, the defined amount of powdered onion peel is mixed with the organic solvent in a proportion of 1-10 g/30 mL (m/v), and stirred for 24 hours at room temperature. The obtained solution is filtered, then evaporated to dryness. The obtained crude extract may be separated by the high-performance liquid chromatography method.

The separation conditions may be as follows:

50 mg to 200 mg of crude extract is injected into a Phenomenex C18 column (21.2 mm×150 mm, 5 μm, 100 A) of the HPLC apparatus. The following solvents may be used: Solvent A: H20/TFA 0.5% (1 L/5 mL); Solvent B: ACN. The flow may be: 15 mL/min.

Qualitative and quantitative analyses of the compositions may be performed by the UPLC-DAD-MS techniques (Agilent technologies, USA). The elution conditions may be as follows: 1 μL of the solution is injected into the Agilent C18 column (2.1 mm, 1.8 μm) of the UPLC at the temperature of 25° C. The solvents used may be: Solvent A: $H_2O$/HCOOH 0.1% and Solvent B: ACN/HCOOH 0.1%. The flow may be: 0.4 mL/min. The isolated compounds may be detected first by the diode array detector, then by the Mass-Spectrometer analyzer. Mass Spectrometry analyses may be performed in negative or positive mode. The separation and analysis techniques by the UPLC-DAD-MS method may be the same for all of the compositions.

According to one embodiment, the composition may be prepared by mixing the commercially-available compounds: quercetin, 2-(3,4-dihydroxybenzoyl)-2,4,6-trihydroxy-3 (2H)-benzofuranone, protocatechuic acid and the salt selected from sodium chloride or potassium chloride.

The dry composition may be prepared by one of the following methods:

a). Dissolution of quercetin, 2-(3,4-dihydroxybenzoyl)-2, 4,6-trihydroxy-3(2H)-benzofuranone, protocatechuic acid and salt in the water heated to 80-100° C. Then the solution is cooled to room temperature, frozen and freeze-dried.

b). Dissolution of quercetin, 2-(3,4-dihydroxybenzoyl)-2, 4,6-trihydroxy-3(2H)-benzofuranone, protocatechuic acid in water heated to 80-100° C. Then the solution is cooled to room temperature, and the salt is added and dissolved. Then the solution is frozen and freeze-dried.

c). Quercetin, 2-(3,4-dihydroxybenzoyl)-2,4,6-trihydroxy-3(2H)-benzofuranone and protocatechuic acid are dissolved in the organic solvent, preferably in ethanol or methanol diluted with water. The organic solvent/water ratio may be between 50/50 and 90/10 (v/v). The salt is dissolved in the water. Then, the two solutions are mixed at room temperature, frozen and freeze-dried.

d). Powders of quercetin, 2-(3,4-dihydroxybenzoyl)-2,4, 6-trihydroxy-3(2H)-benzofuranone and protocatechuic acid are mixed with sodium chloride or potassium chloride.

The composition may be sterilized or not, may be provided in the dry or liquid form, distributed in single-dose or multi-dose containers.

The composition may include one or more biologically active ingredients consistent with therapy and additives selected from pharmaceutical carriers, stabilizers, surfactants, preservatives, and essential oils. The biologically active ingredients may be selected from antibiotics, corticosteroids, and/or copper, manganese and sulfur salts. The essential oils may be chosen from eucalyptus oil, rosemary oil, tea tree oil or menthol.

According to one embodiment, the dry composition may subsequently be mixed with water. The obtained solution or suspension comprises sodium chloride and/or potassium chloride in concentration 0.4-2% by weight, quercetin in concentration 0.0023-0.03% by weight, 2-(3,4-dihydroxybenzoyl)-2,4,6-trihydroxy-(2H)-benzofuranone in concentration 0.00000001-0.03% by weight and protocatechuic acid in concentration 0.00000001-0.03% by weight.

According to another embodiment, the dry composition may be mixed with the solution containing the bicarbonate salt. The bicarbonate salt may be sodium bicarbonate or potassium bicarbonate or both. The bicarbonate salt concentration may vary up to 0.5%, preferably between 0.1%-0.5% by weight, more preferably 0.25-0.5% by weight. The temperature of the water or bicarbonate solution may be between 30° C. and 38° C. At this temperature, certain compounds, for example quercetin, may remain in suspension, others may be dissolved completely. According to one embodiment, the water may be boiled and then cooled to 37° C. before mixing.

The water used for the preparation of the liquid composition may be distilled, deionized, purified and sterilized.

Although the use of preservatives and other excipients in the composition is not excluded, sterile preparations without preservatives may be produced. This makes it possible to keep the compositions in sterile conditions and to limit the adverse effects due to the presence of preservatives. The blow-fill-seal technique, using unidose plastic containers or pre-filled syringes under aseptic conditions, may be preferred.

In one embodiment, the composition may be presented as follows:

Composition consisting of two parts:
part A: containing the dry powder, comprising sodium chloride or potassium chloride, quercetin, 2-(3,4-dihydroxybenzoyl)-2,4,6-trihydroxy-3(2H)-benzofuranone and protocatechuic acid.
part B: containing 20 mL of water or sodium bicarbonate or potassium bicarbonate solution.

4. Nasal Composition, Comprising the Salt and Quercetin, Quercetin-4'-Glycoside and 2-(3,4-dihydroxybenzoyl)-2,4,6-trihydroxy-3(2H)-benzofuranone According to one embodiment, the nasal formulation comprises salt and quercetin, quercetin-4'-glycoside and 2-(3,4-dihydroxybenzoyl)-2,4,6-trihydroxy-3(2H)-benzofuranone. The salt may be sodium chloride or potassium chloride, or both, in quantity sufficient to produce the hypotonic, isotonic or hypertonic solution. The amount of salt may be between 91-99.99% by weight of the dry composition. The amount of quercetin in the dry composition may be between 0.000001-3% by weight. The amount of quercetin-4'-glycoside in the dry composition may be between 0.000001-3% by weight. The amount of 2-(3,4-dihydroxybenzoyl)-2,4,6-trihydroxy-3(2H)-benzofuranone in the dry composition may be between 0.000001-3% by weight.

According to one embodiment, the active agent comprising quercetin, quercetin-4'-glycoside and 2-(3,4-dihydroxybenzoyl)-2,4,6-trihydroxy-3(2H)-benzofuranone may be prepared by the method of extraction from plants containing flavonoids, for example from onion peel. The method of preparing the extract containing active agents may comprise the following stages:

mixing the powdered onion peel with cold water in a proportion of 0.1-2 g/50 mL (m/v);
bringing the mixture to a boil, and simmering for 30 min at boiling temperature;
cooling the mixture, filtering and freeze-drying it.

This method makes it possible to obtain a crude extract composed of the active agents: quercetin, 2-(3,4-dihydroxybenzoyl)-2,4,6-trihydroxy-3(2H)-benzofuranone, quercetin-4'-glycoside and protocatechuic acid. The crude extract may also contain other impurities derived from quercetin, for example, quercetin-3'-glycoside, quercetin-7'-glycoside, diglycosides and triglycosides of quercetin, quercetin dimers, in an amount not exceeding 5% of the total weight of active agents.

Another extraction method consists of using of organic solvents, preferably methanol or ethanol diluted with water in a ratio between 50/50 and 90/10 (v/v). According to this method, the defined amount of powdered onion peel is mixed with the organic solvent in a proportion of 1-10 g/30 mL (m/v), and stirred for 24 hours at room temperature. The obtained solution is filtered, then evaporated to dryness. The obtained crude extract may be separated by the high-performance liquid chromatography method.

The separation conditions may be as follows:
50 mg to 200 mg of crude extract is injected into a Phenomenex C18 column (21.2 mm×150 mm, 5 µm, 100 A) of the HPLC apparatus. The following solvents may be used: Solvent A: H20/TFA 0.5% (1 L/5 mL); Solvent B: ACN. The flow may be: 15 mL/min.

Qualitative and quantitative analyses of the compositions may be performed by the UPLC-DAD-MS techniques (Agilent technologies, USA). The elution conditions may be as follows: 1 µL of the solution is injected into the Agilent C18 column (2.1 mm, 1.8 µm) of the UPLC at the temperature of 25° C. The solvents used may be: Solvent A: $H_2O$/HCOOH 0.1% and Solvent B: ACN/HCOOH 0.1%. The flow may be: 0.4 mL/min. The isolated compounds may be detected first by the diode array detector, then by the Mass-Spectrometer analyzer. Mass Spectrometry analyses may be performed in negative or positive mode. The separation and analysis techniques by the UPLC-DAD-MS method may be the same for all of the compositions.

According to one embodiment, the composition may be prepared by mixing the commercially-available compounds: quercetin, quercetin-4'-glycoside and the salt selected from sodium chloride or potassium chloride.

The dry composition may be prepared by one of the following methods:

a). Dissolution of quercetin, 2-(3,4-dihydroxybenzoyl)-2,4,6-trihydroxy-3(2H)-benzofuranone, quercetin-4'-glycoside and salt in water heated to 80-100° C. Then the solution is cooled to room temperature, frozen and freeze-dried.

b). Dissolution of quercetin, 2-(3,4-dihydroxybenzoyl)-2,4,6-trihydroxy-3(2H)-benzofuranone and quercetin-4'-glycoside in water heated to 80-100° C. Then the solution is cooled to room temperature, and the salt is added and dissolved. Then the solution is frozen and freeze-dried.

c). Quercetin, 2-(3,4-dihydroxybenzoyl)-2,4,6-trihydroxy-3(2H)-benzofuranone and quercetin-4'-glycoside are dissolved in the organic solvent, preferably in ethanol or methanol diluted with water. The organic solvent/water ratio may be between 50/50 and 90/10 (v/v). The salt is dissolved in the water. Then, the two solutions are mixed at room temperature, then frozen and freeze-dried.

d). Powders of quercetin, 2-(3,4-dihydroxybenzoyl)-2,4,6-trihydroxy-3(2H)-benzofuranone and quercetin-4'-glycoside are mixed with sodium chloride or potassium chloride.

The composition may be sterilized or not, may be provided in the dry or liquid form, distributed in single-dose or multi-dose containers.

The composition may include one or more biologically active ingredients consistent with therapy and additives selected from pharmaceutical carriers, stabilizers, surfactants, preservatives, and essential oils. The biologically active ingredients may be selected from antibiotics, corticosteroids, and/or copper, manganese and sulfur salts. The essential oils may be chosen from eucalyptus oil, rosemary oil, tea tree oil or menthol.

According to one embodiment, the dry composition may subsequently be mixed with water. The obtained solution or suspension comprises sodium chloride and/or potassium chloride in concentration 0.4-2% by weight, quercetin in concentration 0.00000001-0.03% by weight, quercetin-4'-glycoside in concentration 0.00000001-0.03% by weight, 2-(3,4-dihydroxybenzoyl)-2,4,6-trihydroxy-3(2H)-benzofuranone in concentration 0.00000001-0.03% by weight.

According to another embodiment, the dry composition may be mixed with the solution containing the bicarbonate salt. The bicarbonate salt may be sodium bicarbonate or potassium bicarbonate or both. The bicarbonate salt concentration may vary up to 0.5%, preferably between 0.1%-0.5% by weight, more preferably 0.25-0.5% by weight. The temperature of the water or bicarbonate solution may be between 30° C. and 38° C. At this temperature, certain compounds, for example quercetin, may remain in suspension, others may be dissolved completely. According to one particular variant, the water may be boiled and then cooled to 37° C. before mixing.

The water used for the preparation of the liquid composition may be distilled, deionized, purified and sterilized.

Although the use of preservatives and other excipients in the composition is not excluded, sterile preparations without preservatives may be produced. This makes it possible to keep the compositions in sterile conditions and to limit the adverse effects due to the presence of preservatives. The blow-fill-seal technique, using unidose plastic containers or pre-filled syringes under aseptic conditions, may be preferred.

In one embodiment, the composition may be presented as follows:
Composition consisting of two parts:
part A: containing the dry powder, comprising sodium chloride or potassium chloride, quercetin, 2-(3,4-dihydroxybenzoyl)-2,4,6-trihydroxy-3(2H)-benzofuranone and quercetin-4'-glycoside.
part B: containing 20 mL of water or sodium bicarbonate or potassium bicarbonate solution.

5. The Nasal Composition, Comprising the Salt, Quercetin and 2-(3,4-Dihydroxybenzoyl)-2,4,6-Trihydroxy-3(2H)-Benzofuranone According to one embodiment, the nasal formulation comprises salt, quercetin and 2-(3,4-dihydroxybenzoyl)-2,4,6-trihydroxy-3(2H)-benzofuranone. The salt may be sodium chloride or potassium chloride, or both, in quantity sufficient to produce the hypotonic, isotonic or hypertonic solution. The amount of salt may be between 94-99.99% by weight of the dry composition. The amount of quercetin in the dry composition may be between 0.000001-3% by weight. The amount of 2-(3,4-dihydroxybenzoyl)-2,4,6-trihydroxy-3(2H)-benzofuranone in the dry composition may be between 0.000001-3% by weight.

According to one embodiment, the active agent comprising quercetin and 2-(3,4-dihydroxybenzoyl)-2,4,6-trihydroxy-3(2H)-benzofuranone may be prepared by the method of extraction from plants containing flavonoids, for example from onion peel. The method of preparing the extract containing active agents may comprise the following stages:
  mixing the powdered onion peel with cold water in a proportion of 0.1-2 g/50 mL (m/v);
  bringing the mixture to a boil, and simmering for 30 min at boiling temperature;
  cooling the mixture, filtering and freeze-drying it.

This method makes it possible to obtain a crude extract composed of the active agents: quercetin, 2-(3,4-dihydroxybenzoyl)-2,4,6-trihydroxy-3(2H)-benzofuranone, quercetin-4'-glycoside and protocatechuic acid. The crude extract may also contain other impurities derived from quercetin, for example, quercetin-3'-glycoside, quercetin-7'-glycoside, diglycosides and triglycosides of quercetin, quercetin dimers, in an amount not exceeding 5% of the total weight of active agents.

Another extraction method consists of using of organic solvents, preferably methanol or ethanol diluted with water in a ratio between 50/50 and 90/10 (v/v). According to this method, the defined amount of powdered onion peel is mixed with the organic solvent in a proportion of 1-10 g/30 mL (m/v), and stirred for 24 hours at room temperature. The solution obtained is filtered, then evaporated to dryness. The obtained crude extract may be separated by the high-performance liquid chromatography method.

The separation conditions may be as follows:
50 mg to 200 mg of crude extract is injected into a Phenomenex C18 column (21.2 mm×150 mm, 5 µm, 100 A) of the HPLC apparatus. The following solvents may be used: Solvent A: H20/TFA 0.5% (1 L/5 mL); Solvent B: ACN. The flow may be: 15 mL/min.

Qualitative and quantitative analyses of the compositions may be performed by the UPLC-DAD-MS techniques (Agilent technologies, USA). The elution conditions may be as follows: 1 µL of the solution is injected into the Agilent C18 column (2.1 mm, 1.8 µm) of the UPLC at the temperature of 25° C. The solvents used may be: Solvent A: $H_2O$/HCOOH 0.1% and Solvent B: ACN/HCOOH 0.1%. The flow may be: 0.4 mL/min. The isolated compounds may be detected first by the diode array detector, then by the Mass-Spectrometer analyzer. Mass Spectrometry analyses may be performed in negative or positive mode. The separation and analysis techniques by the UPLC-DAD-MS method may be the same for all of the compositions.

According to one embodiment, the composition may be prepared by mixing the commercially-available compounds: quercetin, 2-(3,4-dihydroxybenzoyl)-2,4,6-trihydroxy-3 (2H)-benzofuranone and the salt selected from sodium chloride or potassium chloride.

The dry composition may be prepared by one of the following methods:
a). Dissolution of quercetin, 2-(3,4-dihydroxybenzoyl)-2,4,6-trihydroxy-3(2H)-benzofuranone and salt in water heated to 80-100° C. Then the solution is cooled to room temperature, frozen and freeze-dried.

b). Dissolution of quercetin and 2-(3,4-dihydroxybenzoyl)-2,4,6-trihydroxy-3(2H)-benzofuranone in water heated to 80-100° C. Then the solution is cooled to room temperature, and the salt is added and dissolved. Then the solution is frozen and freeze-dried.

c). Quercetin and 2-(3,4-dihydroxybenzoyl)-2,4,6-trihydroxy-3(2H)-benzofuranone are dissolved in the organic solvent, preferably in ethanol or methanol diluted with water. The organic solvent/water ratio may be between 50/50 and 90/10 (v/v). The salt is dissolved in the water. Then, the two solutions are mixed at room temperature, then frozen and freeze-dried.

d). Powders of quercetin and 2-(3,4-dihydroxybenzoyl)-2,4,6-trihydroxy-3(2H)-benzofuranone are mixed with sodium chloride or potassium chloride.

The composition may be sterilized or not, may be provided in the dry or liquid form, distributed in single-dose or multi-dose containers.

The composition may include one or more biologically active ingredients consistent with therapy and additives selected from pharmaceutical carriers, stabilizers, surfactants, preservatives, and essential oils. The biologically active ingredients may be selected from antibiotics, corticosteroids, and/or copper, manganese and sulfur salts. The essential oils may be chosen from eucalyptus oil, rosemary oil, tea tree oil or menthol.

According to one embodiment, the dry composition may subsequently be mixed with water. The obtained solution or suspension comprises sodium chloride and/or potassium chloride in concentration 0.4-2% by weight, quercetin in concentration 0.00000001-0.03% by weight, 2-(3,4-dihydroxybenzoyl)-2,4,6-trihydroxy-3(2H)-benzofuranone in concentration 0.00000001-0.03% by weight.

According to another embodiment, the dry composition may be mixed with the solution containing the bicarbonate salt. The bicarbonate salt may be sodium bicarbonate or potassium bicarbonate or both. The bicarbonate salt concentration may vary up to 0.5%, preferably between 0.1%-0.5% by weight, more preferably 0.25-0.5% by weight. The temperature of the water or bicarbonate solution may be between 30° C. and 38° C. At this temperature, certain compounds, for example quercetin, may remain in suspension, others may be dissolved completely. According to one particular variant, the water may be boiled and then cooled to 37° C. before mixing.

The water used for the preparation of the liquid composition may be distilled, deionized, purified and sterilized.

Although the use of preservatives and other excipients in the composition is not excluded, sterile preparations without preservatives may be produced. This makes it possible to keep the compositions in sterile conditions and to limit the adverse effects due to the presence of preservatives. The blow-fill-seal technique, using unidose plastic containers or pre-filled syringes under aseptic conditions, may be preferred.

In one embodiment, the composition may be presented as follows:

Composition consisting of two parts:
  part A: containing the dry powder, comprising sodium chloride or potassium chloride, quercetin and 2-(3,4-dihydroxybenzoyl)-2,4,6-trihydroxy-3(2H)-benzofuranone.
  part B: containing 20 mL of water or sodium bicarbonate or potassium bicarbonate solution.

The invention is now illustrated by examples and tests on the effectiveness of the invention in the treatment of rhinosinusitis.

EXAMPLES

Example 1

Extraction from Onion Peel.

40 g of ground onion peel was mixed with 2 L of cold water, heated to boiling and kept simmering for 30 min at boiling temperature. The mixture was cooled, filtered and freeze-dried. 5.0 g of dry extract was obtained.

Ethanol Extraction.

200 g of ground onion peel was mixed with 6 L of EtOH/$H_2O$ (70/30; v/v) and left mixed for 24 hours at room temperature. The obtained solution was filtered, then evaporated to dry. 25.5 g of dry extract was obtained.

The qualitative and quantitative analysis of both extracts was performed using UPLC-DAD-MS (Agilent technologies, USA) techniques. Elution conditions: 1 µL of the solution was injected into UPLC column Agilent C18 (2.1 mm, 1.8 µm) at the temperature of 25° C. The solvents used were: Solvent A: $H_2O$/HCOOH 0.1% and Solvent B: ACN/HCOOH 0.1%. Flow: 0.4 mL/min. The separated compounds were detected first by diode array detector (DAD), then analyzed by mass spectrometry methods. The mass spectrometry analyses were performed in positive and negative modes.

The LC-MS spectra were acquired in "Full scan" on the totality of masses (m/z) ranging from 100 to 1400. The obtained data was collected and analyzed by the Hystar software, version 3.0.

The results of the qualitative and quantitative analyses of the alcoholic and water extracts obtained from onion peel are presented in Tables 1 and 2.

TABLE 1

Qualitative and quantitative characteristics of the water extract from onion peel

| Retention time (min) | Mm (Da) | Compound | Content (%) |
| --- | --- | --- | --- |
| 6.7 | 302 | quercetin | 4.85 ± 0.05 |
| 5.5 | 464 | quercetin-4'-glycoside | 2.83 ± 0.05 |
| 3.0 | 154 | protocatechuic acid | 7.22 ± 0.17 |
| 4.1 | 626 | quercetin-diglycoside | 0.16 ± 0.003 |
| 4.3 | 626 | quercetin-diglycoside | 0.2 ± 0.01 |

TABLE 2

Qualitative and quantitative characteristics of the alcoholic extract from onion peel.

| Retention time (min) | Mm (Da) | Compound | Content (%) |
| --- | --- | --- | --- |
| 3.0 | 154 | protocatechuic acid | 2.72 ± 0.08 |
| 4.1 | 626 | quercetin diglycoside | 0.130 ± 0.001 |
| 4.3 | 626 | quercetin diglycoside | 0.262 ± 0.001 |
| 5.5 | 464 | quercetin-4'-glycoside | 2.58 ± 0.04 |
| 6.5 | 454 | quercetin + protocatechuic acid | 0.320 ± 0.002 |
| 6.5 | 454 | quercetin + protocatechuic acid | 0.241 ± 0.003 |
| 6.7 | 302 | quercetin | 6.08 ± 0.31 |
| 6.9 | 764 | quercetin-quercetin glycoside | 0.45 ± 0.02 |
| 7.2 | 764 | dimer of quercetin + glycoside | 0.57 ± 0.02 |
| 7.8 | 602 | quercetin dimer | 1.28 ± 0.04 |
| 8.2 | 902 | quercetin trimer | 0.52 ± 0.02 |

Example 2

Isolation of Pure Compounds.

The crude alcohol extract was separated by the HPLC technique.

50 mg to 200 mg of crude extract was injected into a C18 Phenomenex column (21.2 mm×150 mm, 5 µm, 100 A) of the HPLC apparatus. The solvents used were: Solvent A: $H_2O$/TFA 0.5% (1 L/5 mL); Solvent B: ACN. Flow: 15 mL/min.

Three major compounds were isolated:

1. Protocatechuic acid (98.6% purity), 92.5 mg;
2. Quercetin (98.9% purity) 295 mg;
3. Quercetin-4'-glycoside (96.5% purity), 143 mg.

Processes for preparing the compositions.

1.

40 mg of quercetin and 3 g of NaCl were mixed with 150 mL of boiling water. Then the solution was cooled, frozen and freeze-dried. The obtained powder was distributed by 197.6 mg in unidose containers under sterile conditions.

2.

40 mg of quercetin was mixed with 150 mL of boiling water. Then the solution was cooled, and 3 g of NaCl was added and dissolved. The obtained solution was frozen and freeze-dried. The obtained powder was distributed by 197.6 mg in unidose containers under sterile conditions.

3.

50 mg of quercetin was dissolved in 50 mL of MeOH/$H_2O$ (50/50: v/v). 3.75 g of NaCl was dissolved in 150 mL of $H_2O$. The two obtained solutions were mixed together at room temperature, then frozen and freeze-dried. The obtained powder was distributed by 200 mg in unidose containers under sterile conditions.

4.

40 mg of quercetin was mixed with 3 g of NaCl. The obtained powder was distributed by 200 mg in unidose containers under sterile conditions.

Example 3

Solvent Preparations.

Three different solvents were prepared:

1. 0.625 g of NaCl was dissolved in 250 mL of distilled water. The obtained solution has been sterilized by filtration through a filter with a pore diameter of 0.22 μm and distributed in unidose containers under sterile conditions.

2. 0.625 g of $NaHCO_3$ was dissolved in 250 mL of distilled water. The obtained solution has been sterilized by filtration through a filter with a pore diameter of 0.22 μm and distributed in unidose containers under sterile conditions.

3. Distilled water was dispensed in unidose containers under sterile conditions.

Formulations.

Based on the experimental results described in examples 1 and 2, the initial quantities of active ingredients extracted from onion peel water in 20 mL (the volume for single use) were determined as:
  onion peel extract—10 mg/20 mL;
  quercetin—0.485 mg/20 mL;
  quercetin-4'-glycoside—0.283 mg/20 mL;
  protocatechuic acid—0.722 mg/20 mL.

Different pharmaceutical compositions were formulated using water, NaCl or NaCl+$NaHCO_3$ and active agents (onion peel extract, quercetin, 2-(3,4-dihydroxybenzoyl)-2,4,6-trihydroxy-3(2H)-benzofuranone, quercetin-4'-glycoside or protocatechic acid).

Qualitative and quantitative characteristics of quercetin used for the experimentation were the following:
  quercetin—98%;
  2-(3,4-dihydroxybenzoyl)-2,4,6-trihydroxy-3(2H)-benzofuranone—0.5%;
  quercetin-4'-glycoside—0.1%.

Results of Tests Demonstrating the Effectiveness of the Invention

Treatment of Rhinosinusitis.

Materials and Methods

Study Design.

42 male rabbits were used in this study. Animals were separated into seven groups, each containing six rabbits. The $1^{st}$ group served as an untreated control, the second group was treated with a 0.9% NaCl solution, and five experimental groups were used to test the different formulations: onion peel extract, quercetin+2-(3,4-dihydroxybenzoyl)-2,4,6-trihydroxy-3(2H)-benzofuranone quercetin, quercetin-4'-glycoside and protocatechuic acid.

Induction of Rhinosinusitis.

Rhinosinusitis was induced by introduction of 100 μL of 1% lipopoysaccharide (LPS) in each nasal cavity of the rabbits for three days (Dong-Hyun Kim et all, 2011).

Compounds.

The following concentrations of composition were tested:
  onion peel water extract—1 mg/mL;
  the mixture of quercetin—0.009 mg/mL and 2-(3,4-dihydroxybenzoyl)-2,4,6-trihydroxy-3(2H)-benzofuranone—0.001 mg/mL;
  quercetin—0.01 mg/mL;
  quercetin-4'-glycoside—0.25 mg/mL;
  protocatechuic acid—0.25 mg/mL.

The compounds were diluted in solutions of 0.9-1% sodium chloride or in the solution containing 0.75% NaCl+0.25% $NaHCO_3$ heated to 37° C. before administration. Except for the mixture of quercetin+2-(3,4-dihydroxybenzoyl)-2,4,6-trihydroxy-3(2H)-benzofuranone, which was suspension, all formulations were slightly opalescent-colored solutions.

Treatment Regimen.

2 mL of the solutions was administered intranasally in each nasal cavity once daily for seven days. In order to get the maximal contact of nasal cavity with the tested substances, rabbits were kept in the "head down" position during administration.

Post-Treatment Examinations.

The day after the last administration of the substances, animals were sacrificed by an overdose of a general anesthetics: Zoletil (Virbac, France) and Rometar (Bioveta, Czech Republic).

The nasal cavities of the animals were subjected to visual examinations immediately after euthanasia.

After macroscopic examinations, the nasal parts of rabbits' heads were fixed in 10% formaldehyde for 24 hours, then decalcified for 14 days in a hydrochloric acid/water (25:1) solution. Then, the noses of the animals were sectioned transversally at four levels: A—at the incisors; B—in a zone posterior to the incisors, C— at the second palatal ridge, and D—at the first premolar tooth. Tissues were then washed with water for 12 hours and embedded in paraffin using conventional methods. Histological sections of 3-5 μm were prepared from these tissues using microtome. In order to examine goblet cells and their glucosamine content, the tissue sections were stained with alcian blue at pH 2.5. Some tissue sections were re-stained with haematoxylin and eosin for further histological examinations.

Morphological investigation of histological preparations was performed using optical microscope CarlZeissAxioScopeA1 (Germany) at magnifications of 25×, 50×, 100×, 200× and 400×. Microphotographs of samples were taken using a digital camera AxioCamlCc 1 and AxioVisionRel.4.8 software (Germany). Morphometric measurements were taken using AxioVisionRel.4.8 software (Germany).

Goblet cells were counted within 1 mm of the respiratory zone of the epithelium.

The appearance, severity of acute catarrhal rhinosinusitis, acute purulent rhinosinusitis and occurrence of post-inflammatory hyperplasia of goblet cells were evaluated by examining the degree of inflammatory lesions in various zones: vestibule, respiratory region, olfactory region and paranasal sinuses.

The degree of epithelial desquamation and mucociliary gland damage was scored along a scale from 0 to 3, where:
  0—absence of damage;
  1—slightly damaged;
  2—moderately damaged;
  3—strongly damaged.

The degree of mononuclear and leukocyte cell infiltration was evaluated by scoring from 0 to 3, where:
  0—no mononuclear cells present in the zone of examination;
  1—1 to 5 mononuclear cells present in the zone of examination;
  2—6 to 10 mononuclear cells present in the zone of examination;
  3—more than 10 mononuclear cells present in the zone of examination.

Statistical analysis.

All data were analyzed using descriptive statistics. The normality of data distribution was verified by Shapiro-Wilks test. In the case of normality, the mean and the standard error of the mean (s.e.m) were calculated and presented in tables together with n (number of values). When the data did not meet the normality criteria, the median and the $1^{st}$ and $3^{rd}$ interquartile ranges were calculated. The differences between groups were analyzed using parametric or non-parametric tests depending on the distribution type. The analysis of normally distributed data was done using the unifactorial dispersion analysis test (ANOVA), and further post-hoc analysis was done using Tukey's method. The data not corresponding to the normal distribution were analyzed using the non-parametric Kruskal-Wallis test, and the differences between groups were analyzed using the Mann-Whitney test. The difference was determined at a significance level of 0.05.

The statistical analysis was done using the Statistica 10.0 software (StatSoftInc, USA).

Results.

Visual Examination Findings.

All of the groups of rabbits exhibited the same signs of rhinitis after the first administration of LPS: sneezing and scratching of the nose, which correspond to the first stage of rhinosinusitis. On the third day of administration, the LPS caused nasal congestion and edema of the mucous membrane in visible zones of nasal cavity. After the first administration of the tested compounds, edema and serous discharges from the nose were observed. On the $9^{th}$ and $10^{th}$ days of investigation, rare cases (1 of 6) of dryness of the nasal cavity and sneezing without discharge were observed in the treated groups.

Histological Examination Findings.

The mucous membrane of the nasal vestibule exhibited the typical histological structure, represented by stratified squamous epithelium, gradually transiting to simple respiratory epithelium.

The inner nose was lined by two types of mucous membranes corresponding to respiratory and olfactory regions. The mucosa of the respiratory region was represented by pseudostratified columnar ciliated epithelium, basement membrane and underlying loose connective tissue. The epithelium of the respiratory region was composed of ciliated epitheliocytes, basal cells and goblet cells. Histochemical staining with alcian blue have revealed the presence of large vesicles containing glucosamine in most goblet cells, which refers to the increased functional activity of these cells. We observed numerous sero-mucinous glands in the basement membrane.

The olfactory region was located in the dorsal nasal turbinate and the roof of the nasal cavity. The olfactory epithelium was formed of supporting cells, olfactory cells and basal cells.

Table 3 presents the morphometric data of the nasal mucosa.

TABLE 3

Results of goblet cell morphometric study (M ± s.e.m. n = 6).

| Rabbit groups | Goblet cells | | |
| --- | --- | --- | --- |
| | Ratio of alcian positive cells to total number of goblet cells, in % | Number of goblet cells on 1 mm of epithelium | Number of alcian positive cells on 1 mm of epithelium |
| Untreated control | 71.4 ± 3.48 | 40.2 ± 4.00 | 28.8 ± 3.57 |
| Placebo-treated | 45.7 ± 9.66 | 34.0 ± 3.46 | 16.0 ± 4.04 |
| Onion peel crude extract | 31.7 ± 7.96* | 49.4 ± 3.11 | 16.8 ± 5.30 |
| Quercetin + 2-(3,4-dihydroxybenzoyl)-2,4,6-trihydroxy-3(2H)-benzofuranone | 31.6 ± 4.80* | 52.4 ± 3.18 | 17.1 ± 3.38 |
| Quercetin | 47.2 ± 12.33 | 43.0 ± 6.46 | 21.3 ± 6.49 |
| Quercetin-4'-glycoside | 35.8 ± 11.13 | 65.6 ± 6.03* | 21.8 ± 6.78 |
| Protocatechuic acid | 35.0 ± 9.01 | 44.0 ± 6.76 | 16.3 ± 5.82 |
| Results of statistical analysis ANOVA | $F_{6,35} = 2.6$ $p < 0.05$ | $F_{6,35} = 4.2$ $p < 0.05$ | $F_{6,35} = 0.8$ $p = 0.6$ |

*statistically significant difference, after Tukey's test.

The primary data met the normal distribution criteria. The unifactorial dispersion analysis test (ANOVA) and further post-hoc analysis done by Tukey's test revealed the following differences (Table 3):

Decrease in the ratio of alcian-positive ells to total number of goblet cells in rabbits after administration of onion peel crude extract and quercetin+2-(3,4-dihydroxybenzoyl)-2,4,6-trihydroxy-3(2H)-benzofuranone compared to control.

Increase in the number of goblet cells on 1 mm of epithelium in rabbits after administration of quercetin-4'-glycoside compared to control.

TABLE 4

Morphometry and evaluation of inflammation (score 0-3) n = 6

| Rabbit groups | Mononuclear infiltrate of mucous membrane | Leukocyte infiltrate of mucous membrane | Mucous gland damage | Epithelial desquamation |
| --- | --- | --- | --- | --- |
| Untreated control | 1.0(1.0; 2.0) | 2.0(1.0; 2.0) | 1.0(0.0; 2.0) | 1.0(1.0; 1.0) |
| Placebo-treated | 1.0(1.0; 2.0) | 2.0(1.0; 2.0) | 1.5(1.0; 2.0) | 1.5(1.0; 2.0) |

TABLE 4-continued

Morphometry and evaluation of inflammation (score 0-3) n = 6

| Rabbit groups | Mononuclear infiltrate of mucous membrane | Leukocyte infiltrate of mucous membrane | Mucous gland damage | Epithelial desquamation |
|---|---|---|---|---|
| Onion peel crude extract | 1.0(1.0; 1.0) | 0.5(0.0; 1.0)* | 0.0(0.0; 1.0) | 0.0(0.0; 1.0) |
| Quercetin + 2-(3,4-dihydroxybenzoyl)-2,4,6-trihydroxy-3(2H)-benzofuranone | 1.0(1.0; 1.0) | 0.5(0.0; 1.0)* | 0.0(0.0; 0.0) | 0.0(0.0; 0.0)* |
| Quercetin | 1.0 (1.0; 1.0) | 2.0(2.0; 2.0) | 0.5(0.0; 2.0) | 0.5(0.0; 1.0) |
| Quercetin-4'-glycoside | 1.0 (1.0; 1.0) | 1.0(1.0; 2.0) | 0.0(0.0; 1.0) | 0.0(0.0; 0.0)* |
| Protocatechuic acid | 1.0 (1.0; 1.0) | 0.5(0.0; 1.0)* | 1.0(0.0; 1.0) | 0.0(0.0; 1.0) |
| Results of statistical analysis (Kruskal-Wallis test) | H (6. N = 42) = 6.8 $p = 0.3$ | H (6. N = 42) = 15.7 $p < 0.05$ | H (6. N = 42) = 10.1 $p = 0.1$ | H (6. N = 42) = 16.8 $p < 0.05$ |

*statistically significant difference, $p < 0.05$; Mann-Whitney test

TABLE 5

Results of the rabbit sino-nasal inflammation study.

| | Inflammation type | | | Inflammation degree in different zones | | |
|---|---|---|---|---|---|---|
| | Post-inflammatory | | | | | |
| Rabbit groups | hyperplasia of goblet cells | acute catarrhal rhinosinusitis | acute purulent rhinosinusitis | Vestibule | Olfactory region | Respiratory region |
| Untreated control | 1.0 (0.0; 1.0) | 1.5 (1.0; 2.0) | 0.0 (0.0; 0.0) | 0.0 (0.0; 0.0) | 1.5 (1.0; 2.0) | 1.5 (1.0; 2.0) |
| Placebo-treated | 0.5 (0.0; 1.0) | 2.0 (1.0; 2.0) | 0.5 (0.0; 1.0) | 0.0 (0.0; 0.0) | 1.5 (0.0; 2.0) | 2.0 (1.0; 2.0) |
| Onion peel crude extract | 1.0 (1.0; 2.0) | 1.0 (0.0; 1.0)* | 0.5 (0.0; 1.0) | 0.0 (0.0; 0.0) | 0.5 (0.0; 1.0) | 1.0 (0.0; 1.0)* |
| Quercetin + 2-(3,4-dihydroxybenzoyl)-2,4,6-trihydroxy-3(2H)-benzofuranone | 1.0 (0.0; 2.0) | 0.5 (0.0; 1.0)* | 0.0 (0.0; 0.0) | 0.0 (0.0; 0.0) | 0.0 (0.0; 0.0) | 1.0 (1.0; 1.0) |
| Quercetin | 0.0 (0.0; 0.0) | 2.0 (2.0; 2.0) | 0.0 (0.0; 0.0) | 0.0 (0.0; 0.0) | 1.0 (0.0; 1.0) | 2.0 (2.0; 2.0) |
| Quercetin-4'-glycoside | 1.0 (1.0; 2.0) | 1.0 (1.0; 2.0) | 0.0 (0.0; 0.0) | 0.0 (0.0; 0.0) | 0.5 (0.0; 1.0) | 1.0 (1.0; 1.0) |
| Protocatechuic acid | 0.5 (0.0; 2.0) | 1.0 (0.0; 1.0) | 0.0 (0.0; 0.0) | 0.0 (0.0; 0.0) | 1.0 (0.0; 2.0) | 1.0 (1.0; 1.0) |
| Results of statistical analysis Kruskal-Wallis test | H (6. N = 42) = 10.5 $p = 0.1$ | H (6. N = 42) = 15.5 $p < 0.05$ | H (6. N = 42) = 17.0 $p < 0.05$ | H (6. N = 42) = 2.2 $p = 0.9$ | H (6. N = 42) = 6.9 $p = 0.3$ | H (6. N = 42) = 18.3 $p < 0.05$ |

*statistically significant difference, $p < 0.05$; Mann-Whitney test

Non-parametrical analysis of the degree of pathological inflammation by scoring from 0 to 3 using the Kruskal-Wallis and Mann-Whitney tests showed the following significant differences between groups:

- in the groups receiving onion peel crude extract, quercetin+2-(3,4-dihydroxybenzoyl)-2,4,6-trihydroxy-3(2H)-benzofuranone or protocatechuic acid, the leucocyte cell infiltration of the mucous membranes was lower than in control group;
- epithelial desquamation was not observed in the groups receiving quercetin+2-(3,4-dihydroxybenzoyl)-2,4,6-trihydroxy-3(2H)-benzofuranone or quercetin-4'-glucoside;
- the degree of inflammatory lesions in the respiratory region was significantly lower in the group receiving onion peel crude extract;
- no sign of post-inflammatory hyperplasia of the goblet cells and acute purulent rhinosinusitis in the group receiving quercetin;
- the frequency of acute catarrhal rhinosinusitis was lower in the groups receiving quercetin+2-(3,4-dihydroxybenzoyl)-2,4,6-trihydroxy-3(2H)-benzofuranone or onion peel crude extract;
- no difference was observed within the groups in the appearance of acute purulent rhinosinusitis.

All goblet cells contain mucopolysaccharides stained by alcian blue. The number of goblet cells is increased during inflammation and must decrease after treatment. From the obtained data, it can be concluded that the proportion of these cells increased significantly after the induction of inflammation. In general, this process is accompanied by infiltration of the mucosa. If there is no infiltration, but the number of goblet cells remains high, this is considered a post-inflammatory hyperplasia, which is a sign of improvement.

Control Group. No Macroscopic Changes were Observed in the Control Group.

The microscopic examinations showed that the administration of LPS caused inflammation in the respiratory and olfactory zones. Edema and leucocyte infiltration in the mucous membranes and underlying tissue were observed in the vestibule. Epithelial desquamation and atrophy of mucous glands were observed in the respiratory zone. Staining with alcian blue revealed clustered hyperplasia zones of goblet cells in the respiratory region. Morphometric evaluation of the epithelium has shown a significant increase of goblet cells containing glucosamines and mucopolysaccharides in relation to the total number of goblet cells. A moderate lymphocyte and macrophage infiltration in mucous membranes and underlying tissues was also observed. Moderate inflammatory changes were found in the vomeronasal organ. Thus, after administration of the pro-inflammatory agent LPS, an acute catarral rhinosinusitis was observed in rabbits (table 5).

The animals in the second group treated with 0.9% sodium chloride solution did not show any macroscopic changes upon visual observation.

The microscopic studies revealed some signs of epithelial desquamation in respiratory and olfactory zones of the mucous membrane, moderate to significant leucocyte infiltration, presence of exudate with elevated amount of neutrophils and cellular debris. The number of alcian-positive cells on 1 mm of epithelium, as well as the number of goblet cells, were lower than in non-treated animals. This was due to the necrotisation of the mucous membrane and inflammatory lesions of the epithelium. In general, the signs of acute catarrhal rhinosinusitis and purulent rhinosinusitis were observed in this group.

Animals in the 3$^{rd}$ and 4$^{th}$ groups receiving onion peel crude extract and quercetin+2-(3,4-dihydroxybenzoyl)-2,4,6-trihydroxy-3(2H)-benzofuranone did not show the signs of disease during macroscopic (visual) examination.

The microscopic examination revealed very mild signs of inflammation compared to the non-treated group. Slight lymphocyte infiltration appeared in the mucous membrane and was practically absent in underlying tissues. No signs of epithelial desquamation were found in these two groups. We observed signs of regeneration in the respiratory and olfactory regions and mucous glands. Some animals had post-inflammatory hyperplasia of goblet cells. Acute purulent rhinosinusitis was absent in the group receiving quercetin+ 2-(3,4-dihydroxybenzoyl)-2,4,6-trihydroxy-3(2H)-benzofuranone.

No external changes were observed after macroscopic examination in animals in the 5$^{th}$, 6$^{th}$ and 7$^{th}$ groups receiving quercetin in NaCl, quercetin-4'-glycoside and protocatechuic acid, respectively.

Microscopic investigations revealed signs of inflammatory process, which were stronger than that of animals receiving onion peel crude extract and quercetin+2-(3,4-dihydroxybenzoyl)-2,4,6-trihydroxy-3(2H)-benzofuranone, but milder than that of non-treated rabbits. No signs of purulent rhinosinusitis were observed in these groups.

CONCLUSION

The results of the histological examination of animals after treatment with onion peel extract and the compounds isolated from it have revealed that the onion peel extract and quercetin+2-(3,4-dihydroxybenzoyl)-2,4,6-trihydroxy-3 (2H)-benzofuranone have shown the best therapeutic effect compared to non-treated or placebo-treated animals. The best therapeutic effect of onion peel crude extract can be explained by the sum of several compounds, each of them demonstrating more or less anti-inflammatory activity and probably having potentiating capacity. Unexpectedly, the mixture of quercetin and 2-(3,4-dihydroxybenzoyl)-2,4,6-trihydroxy-3(2H)-benzofuranone showed the best therapeutic effect in comparison with quercetin alone. This could be explained by two reasons. The first is the presence of 2-(3,4-dihydroxybenzoyl)-2,4,6-trihydroxy-3(2H)-benzofuranone. The second is that quercetin in suspension form could have a long-lasting effect compared to quercetin in solution.

Quercetin-4'-glycoside (GCA) and protocatechuic acid have shown moderate activity against rhinosinusitis. By correlating the doses of each tested substance to the therapeutic effect achieved, we have concluded that quercetin in the form of suspension in solutions containing NaCl or NaCl/NaHCO$_3$ could be the preferred drug for the treatment of acute and chronic rhinosinusitis.

The invention claimed is:

1. A composition for rinsing the nasal cavity and the sinus cavities for curative or prophylactic treatments of acute and/or chronic rhinitis, and acute and chronic sinusitis, comprising:
   sodium chloride and/or potassium chloride;
   quercetin; and,
   2-(3,4-dihydroxybenzoyl)-2,4,6-trihydroxy-3(2H)-benzofuranone;
   wherein the quercetin is in the anhydrous form with an approximate molecular mass of 302 g/mol, or in the form of quercetin hydrate with an approximate molecular mass of 320 g/mol, or in the form of quercetin dihydrate with an approximate molecular mass of 338 g/mol; and
   wherein the composition is an intranasal administration composition.

2. The composition for use according to claim 1, which further includes impurities derived from quercetin, selected from: quercetin-3'-glycoside, quercetin-7'-glycoside, diglycosides and triglycosides of quercetin, dimers of quercetin in an amount not exceeding 5% of the total amount of active agents.

3. The composition for use according to claim 2, comprising 83-99.77% by weight of sodium chloride and/or potassium chloride and the extract of plants containing flavonoids: 0.23-3% by weight of quercetin, 0.000001-3% by weight of quercetin-4'-glycoside, 0.000001-3% by weight of 2-(3,4-dihydroxybenzoyl)-2,4,6-trihydroxy-3 (2H)-benzofuranone and 0.000001-3% by weight of protocatechuic acid, and impurities, derived from quercetin in an amount up to 5% by total mass of the active agents; and wherein the composition is in dry powder form.

4. A solution or suspension comprising the composition according to claim 3 and water, wherein the solution or suspension comprises 0.4-2% by weight of sodium chloride and/or potassium chloride, 0.0023-0.03% by weight of quercetin, 0.00000001-0.03% by weight of quercetin-4'-glycoside, 0.00000001-0.03% by weight of 2-(3,4-dihydroxybenzoyl)-2,4,6-trihydroxy-3(2H)-benzofuranone and 0.00000001-0.03% by weight of protocatechuic acid and impurities, derived from quercetin up to 0.5% by total weight of active agents.

5. The composition for use according to claim 1, comprising 94-99.99% by weight of sodium chloride and/or potassium chloride, 0.000001-3% by weight of quercetin, and 0.000001-3% by weight of 2-(3,4-dihydroxybenzoyl)-2,4,6-trihydroxy-3(2H)-benzofuranone, and wherein the composition is in dry powder form.

6. A solution or suspension comprising the composition according to claim 5 and water, wherein the solution or suspension contains 0.4-2% by weight of sodium chloride and/or potassium chloride, 0.00000001-0.03% by weight of quercetin and 0.00000001-0.03% by weight of 2-(3,4-dihydroxybenzoyl)-2,4,6-trihydroxy-3(2H)-benzofuranone.

7. The solution or suspension according to claim 6, which further comprises sodium bicarbonate or potassium bicarbonate or a mixture of both up to 0.5% by weight.

8. The solution or suspension according to claim 6, which further comprises one or more therapeutic ingredients selected from antibiotics, corticosteroids and/or copper, manganese and sulfur salts, essential oils and excipients selected from pharmaceutical carriers, stabilizers, surfactants, preservatives.

9. The composition for use according to claim 1, comprising 91-99.99% by weight of sodium chloride and/or potassium chloride, 0.000001-3% by weight of quercetin, 0.000001-3% by weight of 2-(3,4-dihydroxybenzoyl)-2,4,6-trihydroxy-3(2H)-benzofuranone, and wherein the composition further comprises 0.000001-3% by weight of quercetin-4'-glycoside; and wherein the composition is in dry powder form.

10. A solution or suspension comprising the composition according to claim 9 and water, wherein the solution or suspension comprises 0.4-2% by weight of sodium chloride and/or potassium chloride, 0.00000001-0.03% by weight of quercetin, 0.00000001-0.03% by weight of 2-(3,4-dihydroxybenzoyl)-2,4,6-trihydroxy-3(2H)-benzofuranone and 0.00000001-0.03% by weight of quercetin-4'-glycoside.

11. The dry composition for use according to claim 1, comprising 91-99.77% by weight of sodium chloride and/or potassium chloride, 0.23-3% by weight of quercetin, 0.000001-3% by weight of 2-(3,4-dihydroxybenzoyl)-2,4,6-trihydroxy-3(2H)-benzofuranone, and wherein the composition further comprises 0.000001-3% by weight of protocatechuic acid; and wherein the composition is in dry powder form.

12. A solution or suspension comprising the composition according to claim 11 and water, wherein the solution or suspension comprises 0.4-2% by weight of sodium chloride and/or potassium chloride, 0.0023-0.03% by weight of quercetin, 0.00000001-0.03% by weight of 2-(3,4-dihydroxybenzoyl)-2,4,6-trihydroxy-3(2H)-benzofuranone and 0.00000001-0.03% by weight of protocatechuic acid.

13. The composition of claim 1, wherein the composition further comprises quercetin-4'-glycoside and/or protocatechuic acid.

14. A method of prophylaxis and treatment of acute and chronic rhinitis and/or acute and chronic sinusitis, the method comprising rinsing the nasal cavity and the sinus cavities of a subject in need thereof with the solution or suspension of claim 6.

15. A method of preparation of the composition according to claim 1, comprising:
  a). dissolving sodium chloride or potassium chloride and at least the following active agents: quercetin and 2-(3,4-dihydroxybenzoyl)-2,4,6-trihydroxy-3(2H)-benzofuranone in water heated to 80-100° C., cooling, freezing and freeze-drying the solution; or
  b). dissolving in water heated to 80-100° C. at least the following active agents: quercetin and 2-(3,4-dihydroxybenzoyl)-2,4,6-trihydroxy-3(2H)-benzofuranone, cooling the solution, adding sodium chloride or potassium chloride to the solution after cooling, and mixing, freezing and freeze-drying the mixture; or
  c). dissolving at least the following active agents: quercetin and 2-(3,4-dihydroxybenzoyl)-2,4,6-trihydroxy-3(2H)-benzofuranone in an organic solvent, ethanol or methanol diluted with water, wherein the organic solvent/water ratio is between 50/50 and 90/10; dissolving sodium chloride or potassium chloride in water, mixing the two solutions at room temperature, and freezing and freeze-drying the mixture; or
  d). mixing the following compounds in powder form: active agents including quercetin and 2-(3,4-dihydroxybenzoyl)-2,4,6-trihydroxy-3(2H)-benzofuranone with sodium chloride or potassium chloride;
  wherein the method further comprises obtaining the active agents for steps a), b), c) or d) by performing at least the following steps:
  mixing powdered onion peel with cold water in proportion 0.1-2 g/50 mL,
  bringing the mixture to a boil,
  simmering the mixture at boiling temperature,
  cooling, filtering and freeze-drying the mixture.

* * * * *